United States Patent [19]

Henfrey

[11] Patent Number: 4,934,392
[45] Date of Patent: Jun. 19, 1990

[54] CLEANING APPARATUS

[75] Inventor: Kenneth M. Henfrey, Berkshire, United Kingdom

[73] Assignee: Shubert Systems Limited, Havant, United Kingdom

[21] Appl. No.: 122,408

[22] Filed: Nov. 19, 1987

[51] Int. Cl.⁵ .......................... B08B 3/00; A61L 2/00
[52] U.S. Cl. ..................... 134/61; 134/107; 134/186; 134/25.4; 422/302
[58] Field of Search .............. 134/25.4, 61, 66–81, 134/107, 186, 84, 88, 90, 91; 422/292, 302, 304; 406/124, 127, 191, 192

[56] References Cited

U.S. PATENT DOCUMENTS

| | | | |
|---|---|---|---|
| 2,499,891 | 3/1950 | Wagner | 134/61 X |
| 3,455,644 | 7/1969 | Arber | 422/302 |
| 4,304,611 | 12/1981 | Ellis | 134/72 X |
| 4,670,935 | 6/1987 | Bowler | 134/67 X |

FOREIGN PATENT DOCUMENTS

| | | | |
|---|---|---|---|
| 2754726 | 6/1978 | Fed. Rep. of Germany | 134/25.4 |
| 2801568 | 7/1979 | Fed. Rep. of Germany | 422/302 |
| 257989 | 8/1971 | U.S.S.R. | 134/69 |
| 589034 | 2/1978 | U.S.S.R. | 134/61 |
| 1044680 | 9/1983 | U.S.S.R. | 134/84 |
| 1076385 | 2/1984 | U.S.S.R. | 406/127 |
| 5222 | of 1902 | United Kingdom | 134/66 |

Primary Examiner—Harvey C. Hornsby
Assistant Examiner—Stephen F. Gerrity
Attorney, Agent, or Firm—Allegretti & Witcoff, Ltd.

[57] ABSTRACT

There is described a cleaning apparatus, suitable for cleaning components for pharmaceutical containers, such as for example pharmaceutical closures, which comprises a plurality of processing chambers interconnectible by valve means capable of providing a bacteriological barrier between the first and last chambers. Typically, the apparatus may be arranged to wash, dry and sterilize the container components.

14 Claims, 3 Drawing Sheets

CLEANING APPARATUS

FIELD OF THE INVENTION

The present invention relates to a cleaning apparatus for pharmaceutical container components, in particular for pharmaceutical closures such as for example aluminium caps, rubber or plastics stoppers, and rubber or plastics seals.

DESCRIPTION OF PRIOR ART

Before pharmaceuticals containers are filled, the container components generally have to be cleaned and sterilized.

Up to now, component washing, drying and sterilization has either been performed in separate machines, which requires the operator to provide means for sterile transfer of the components between the machines, or in large, complex and expensive machines which are designed to process the components in batches in a single processing chamber in which washing, drying and sterilizing, and other optional handling operations such as silicone treatment, are all performed. In general, these processing chambers have been rotatable pressure vessels which are expensive to construct and require complex mounting and drive mechanisms.

Typical among known pharmaceutical component cleaning and sterilizing apparatus are the WTS and WPS machines produced by Anton Huber GmbH & Co. KG of Freising, West Germany, the PHARMA-CLEAN SST-BSA machines produced by Pharmatechnik SMEJA GmbH & Co. KG of Straelen-Herongen, West Germany, and the LST machines produced by NICOMAC SRL of Milan, Italy.

As mentioned above, machines for washing pharmaceutical components for subsequent drying and sterilization in separate apparatus are known. Thus, for example, Paxall Schubert Machinery Co. A/S of Denmark produce a washing machine capable of performing the washing operation in a chamber having a single component inlet/outlet aperture; with this machine the actual washing operation is effected by air agitation of a liquid cleansing medium within the chamber. The washed components are then lifted out of the chamber for subsequent sterilization in a separate apparatus.

I have now found that, by the use of a plurality of component processing chambers selectively interconnectible by valve means capable of providing a bacteriological barrier between the cleaning chamber and subsequent chambers, disadvantages of the prior art apparatus may be avoided.

SUMMARY OF THE INVENTION

Viewed from one aspect the invention therefore provides a pharmaceutical container component cleaning apparatus comprising a first chamber arranged to receive pharmaceutical container components for cleaning and provided with cleaning means, a second chamber arranged to sterilize pharmaceutical container components cleaned in said first chamber and provided with sterilizing means, and valve means operable to permit transfer of cleaned components from said first chamber to said second chamber and closeable to provide a bacteriological barrier between said first and second chambers.

Viewed from a further aspect, the invention also provides a process for cleaning pharmaceutical container components comprising:

(i) loading pharmaceutical container components into a cleaning chamber having a sealable valve means;

(ii) cleaning said components in a cleaning medium in said cleaning chamber and thereafter draining said medium from said cleaning chamber;

(iii) passing said components through said sealable valve means and into a sterilizing chamber;

(iv) sterilizing said components in said sterilizing chamber; and (v) removing said components from said sterilizing chamber.

The valve means in the apparatus of the invention preferably comprises a displaceable valve plate, a displaceable annular seal member, valve plate displacing means operable to move the valve plate between an open position permitting passage of components through the valve means and a closed position preventing such passage, and seal member displacing means operable to urge the seal member into sealing engagement with the valve plate when the valve plate is in its closed position.

This valve construction, since it allows the valve plate to be moved between its open and closed positions without rubbing against other elements of the valve assembly or housing, is not prone to leakage due to abrasion and is thus generally applicable to pharmaceutical container component cleansing apparatus. Thus viewed from a still further aspect the invention also provides a pharmaceutical container component cleaning apparatus comprising a first chamber arranged to receive pharmaceutical container components for cleaning and provided with cleaning means, a second chamber arranged to receive pharmaceutical container components cleaned in said first chamber, and valve means operable to permit transfer of cleaned components from said first chamber to said second chamber and closeable to provide a bacteriological barrier between said first and said second chambers, said valve means comprising a displaceable valve plate, a displaceable annular seal member, valve plate displacing means operable to move said valve plate between an open position permitting passage of components through the valve means and a closed position preventing such passage, and seal member displacing means operable to urge said seal member into sealing engagement with said valve plate when said valve plate is in its closed position.

DETAILED DESCRIPTION OF THE INVENTION

Figure 1:
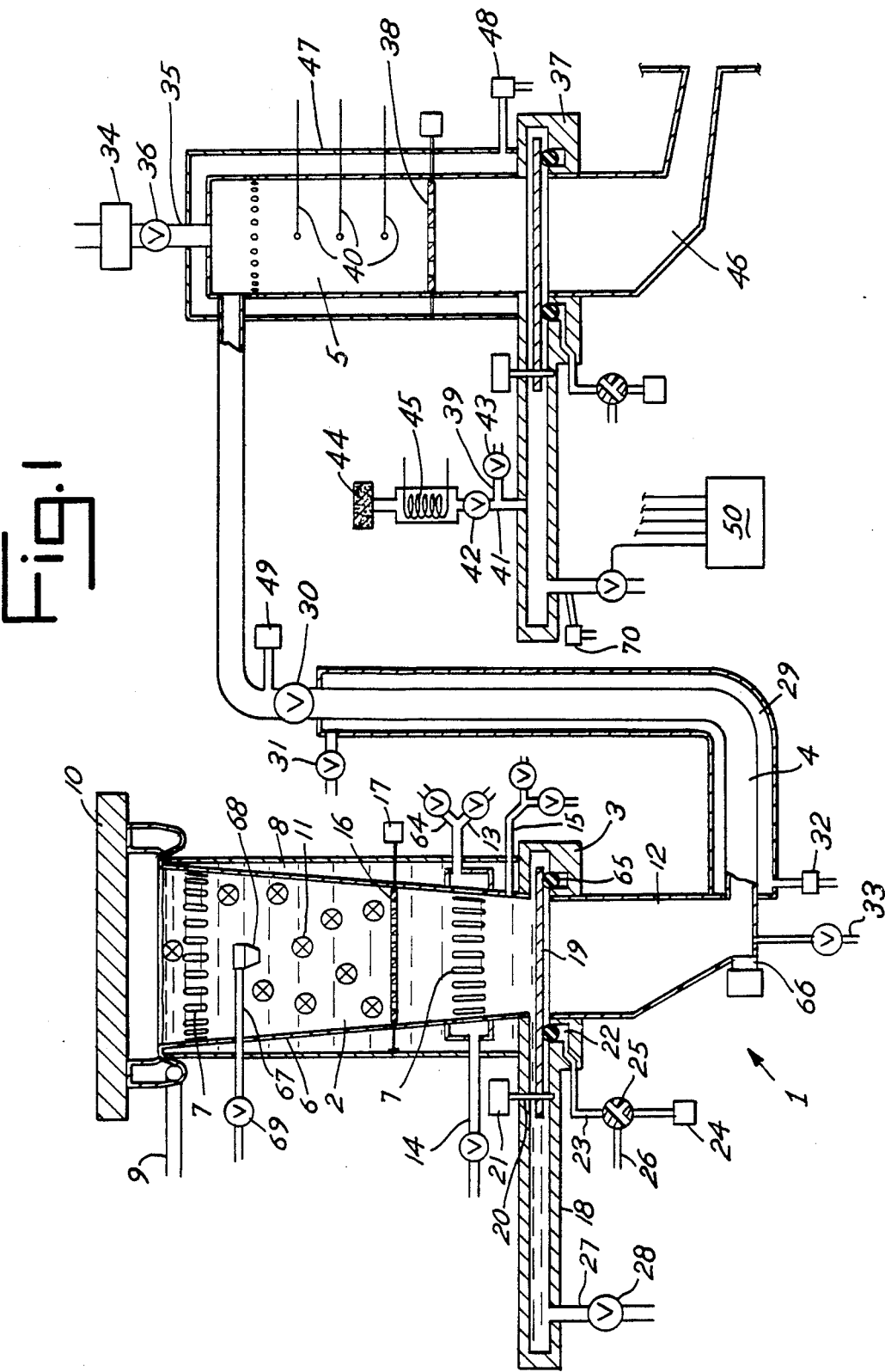
FIG. 1 is a schematic cross-sectional view of one embodiment of a cleaning and sterilizing apparatus according to the present invention.

In one preferred embodiment, the cleaning and sterilizing apparatus according to the invention is provided with a conduit arranged between the first and second chambers and with means for establishing a pressure differential along the conduit whereby to urge components passing through the valve means along the conduit towards the second chamber. By arranging the conduit so that at least part of it is upwardly directed, it is possible not only to arrange the first and second chambers in a side-by-side fashion (thereby reducing the overall height of the apparatus) but also to avoid the need for a separate drying chamber since the tumbling action of the components as they are driven upwards in the conduit throws excess liquid from their surfaces onto the inner surface of the conduit along which inner surface the liquid is then driven by the gas flow. Furthermore, by providing the conduit with heating means to heat its inner wall, the evaporation of the liquid film thereon can be ensured and the temperature of the components on their way to the sterilization chamber can be maintained or even raised to or towards the sterilization temperature.

In another preferred embodiment, the cleaning and sterilizing apparatus of the invention comprises at least three selectively interconnectible chambers with valve means provided between each mutually interconnectible pair of chambers, these valve means being openable to permit components to pass between adjacent chambers and closeable to provide a bacteriological barrier between adjacent chambers. In this way, by suitably controlling the operation of the valve means, a microbiological barrier can be maintained at all times between the cleaning chamber and the sterilizing chamber.

Where the apparatus contains three or more chambers, these may for example be connected via conduits or, in one preferred arrangement, these may be arranged to permit direct gravity feed of components from one chamber to the next. In such a gravity fed arrangement however it will generally be preferred to have a drying chamber interposed between the cleaning and sterilizing chambers.

One or more of the valve means in the apparatus of the invention, and particularly the valve means for component discharge from the cleaning chamber, preferably comprises a displaceable valve plate, a displaceable annular seal member, a valve plate displacing means and a seal member displacing means as discussed above. In a preferred valve design, the valve plate and the seal member are displaceable in mutually perpendicular directions; thus for example the valve plate may be rotatable in the plane of its major surface while the seal member, which may for example be an inflatable seal or an O-ring seated in a pressurizable channel, may be caused to move into contact with the valve plate in a direction perpendicular to that plane.

Where a such valve means is situated at the base of a chamber, it is also preferably provided with a drainage port by means of which liquid in the chamber may be drained away from the chamber and the valve.

In this manner, even with a non-rotating cleaning chamber, it is possible to ensure that the cleaned components discharged from the cleaning chamber do not contact any surfaces which have not been cleaned to the same degree as have the components themselves. For this reason, such a valve assembly is useful even in the case of cleaning apparatus which is not equipped for subsequent component sterilization.

Preferred embodiments of the invention will now be described further with reference to the accompanying drawings.

Referring to FIG. 1, there is shown a cleaning and sterilizing apparatus 1 comprising a cleaning chamber 2, valve means 3, conduit 4 and sterilizing chamber 5.

The cleaning chamber 2 is double walled having an inner sleeve 6 with apertures 7 about its upper and lower peripheries through which cleaning or rinsing medium 8 may pass in the circulation of the cleaning medium in the chamber. Excess liquid and particulate waste may be carried over weir-like upper rim of sleeve 6 to be voided through duct 9. The chamber has an openable lid 10 covering an upper aperture through which components 11 may be introduced for cleaning. The lower end of the cleaning chamber 2 communicates with hopper 12 via valve means 3. The cleaning chamber is provided near its base with steam, air and water inlet ducts 64, 13 and 14 and also with detergent and silicone dosing duct(s) 15. The chamber is further provided with clean water supply duct 67 which protrudes into the upper part of the chamber and terminates with a spray nozzle 68. Within inner sleeve 6, there is disposed a displaceable component support 16, for example a rotatable apertured plate or grid, which is itself provided with drive means 17 capable of moving the support 16 between a position in which it prevents components falling to the base of the cleaning chamber and a position in which it permits the components to pass to the base of the chamber.

The valve means 3 at the base of the cleaning chamber comprises a valve housing 18 containing a valve plate 19 which is rotatable about pivot 20 under the action of drive means 21, and an O-ring 65 seated in an annular groove 22 and displaceable in the vertical direction under the action of gas pressure applied within groove 22 by means of gas supply line 23. The supply line 23 leads to a pressurized gas source 24 and is provided with a 3-way valve 25 whereby groove 22 may be connected to gas supply 24 or to duct 26 (which vents to the atmosphere or is connected to a vacuum pump) to raise or lower O-ring 65 respectively. Valve means 3 is also provided with a drainage duct 27 which itself is provided with a valve 28.

Components leaving the cleaning chamber 2 enter hopper 12 and are fed by motorized feed regulator 66 into conduit 4 which is provided with steam heating jacket 29 and valve 30. Jacket 29 is heated by steam entering at valve 31, the condensate being removed by trap 32. Any excess liquid entering hopper 12 may be drained therefrom by suction line 33. The components are caused to move along conduit 4 through valve 30 and into sterilizing chamber 5 under the action of a pressure differential created by vacuum pump 34 which is connected to the sterilizing chamber by duct 35 and valve 36.

The sterilizing chamber 5 is provided at its base with a valve means 37 and is also provided with a displaceable component support 38. Valve means 37 and support 38 are substantially similar in construction to the valve means 3 and support 16 described above. The sterilizing chamber is also provided with a steam inlet duct 39, temperature sensing probes 40, and air inlet duct 41. The air and steam inlet ducts are provided with valves 42 and 43, and the air inlet duct is also provided with a filter 44 and a heater 45.

The component discharge valve for the sterilizing chamber is valve means 37 and when this is opened sterilized components may pass into a delivery hopper 46.

To perform a cleaning operation in the cleaning chamber 2, steam (e.g. at an inlet pressure of 1-3.5bar, preferably about 2 bar) is first admitted into the steam jackets of the apparatus until they stabilize to the desired temperature (for example about 121° C.), the support 16 is set to its horizontal position, valve means 3 is closed, lid 10 is opened, the chamber 2 is charged with components for cleaning, for example rubber stoppers or aluminium caps, and the wash cycle is begun.

The washing process may consist of water fill through duct 14 (e.g. at a water inlet pressure of 1-3 bar) followed by heating, for example by steam injection through duct 64, and then agitation by compressed air introduced through duct 13 (e.g. at a supply pressure of 4-6 bar) with or without the introduction of detergent through duct 15. This is followed by rinsing. In the washing and rinsing operations, clean water is introduced either continuously or at intervals with soiled cleaning medium being discharged through ducts 9 and 27. On completion of the washing or rinsing cycles, valve 28 is opened and the liquid is drained away through the drainage duct 27.

After the washing, heating, rinsing, draining and optional other treatments (e.g. silicone treatment) of the components in cleaning chamber 2, the 3-way valve 25 is operated to vent groove 22 to lower O-ring 65 and valve plate 19 is rotated to its open position and support 16 is rotated to allow the cleaned components to fall into hopper 12. To prevent the components from sticking to the sides of the cleaning chamber, valve 69 is opened and a fine spray of clean water, e.g. demineralized water, is directed through nozzle 68 onto the contents of the chamber.

If desired, before and/or after the components are cleaned, the valve means 3 may itself be subjected to a further cleaning and rinsing operation in which the water level within the chamber is not allowed to rise up to the support 16.

For the delivery of components from hopper 12 to the sterilizing chamber 5, the valve means 37 is closed, support 38 is set to its horizontal position, valves 42 and 43 are closed, feed regulator 66 and pump 34 are actuated and valves 30 and 36 are opened.

When the transfer of components into the sterilizing chamber is complete, valve 30 and valve means 3 are closed and the cleaning chamber can be loaded with a fresh charge of components and the cleaning of these new components can begin.

For the sterilization of the components in the sterilization chamber 5, valve 36 is kept open until the desired vacuum in the chamber is reached. Valve 43 is then opened to admit steam through duct 39 and after a period when any remaining air is purged through pump 34, valve 36 is closed and the temperature in the chamber is allowed to rise to the desired sterilizing temperature, for example 121° C.

The sterilizing chamber is provided with a jacket 47 to minimize condensation but any condensate may be drawn off through trap 70. Any residual air or other condensibles can also be removed by trap 49. Jacket 47 is itself provided with a trap 48 for the removal of condensates.

When the temperature in the sterilizing chamber reaches the sterilizing temperature, a timed period commences during which probes 40 may provide data regarding treatment conditions to an indicator or recorder as required. At the end of the sterilizing period, pump 34 is actuated and valve 36 is opened. When the pressure in the sterilizing chamber reaches ambient pressure, valve 42 is opened to admit filtered and heated air into the chamber. During this period, it is advantageous to close valve 42 from time to time to reduce the pressure in the sterilizing chamber since the rush of air through the chamber when valve 42 is reopened tends to re-locate the components and to ensure their even drying. At the end of the drying period, valve 36 is closed and pump 34 stopped and the pressure in the sterilizing chamber is allowed to return to ambient via valve 42. Valve means 37 is then actuated to move the valve plate to the open position and support 38 is rotated to deposit the sterilized components into the delivery hopper 46. Valve In practice, it is desirable that the surfaces contacted by the components are smooth and durable and thus it is particularly preferred that these surfaces be of stainless steel. It is also preferred that the valves and the other moving parts be operated in the desired sequence and at the desired times by remote actuators under the control of a control means 50 which is capable of automatic operation.

Figure 2:
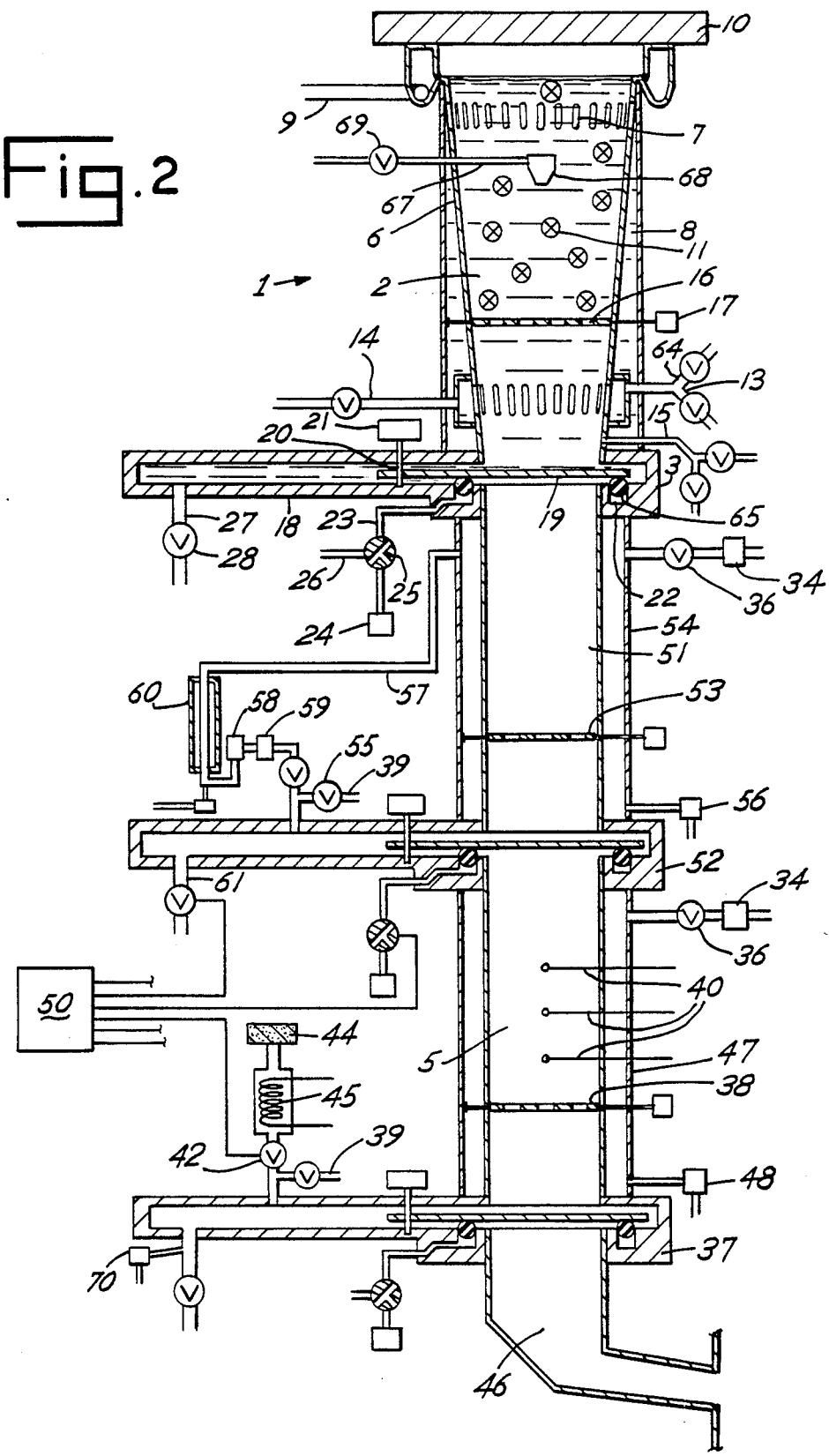
FIG. 2 is a schematic cross-sectional view of a further embodiment of a cleaning and sterilizing apparatus according to the present invention.

Turning to FIG. 2, there is there shown a further cleaning and sterilizing apparatus according to the present invention. In FIG. 2, elements equivalent to elements illustrated in FIG. 1 are similarly numbered. In the apparatus of FIG. 2, the components are fed from the cleaning chamber 2 into a sterilizing chamber 5 via an intermediately positioned drying chamber 51 with component feed between the adjacent chambers being through valve means 3 and 52 and under the action of gravity. The drying chamber 51 is provided with valve means 52 and support 53 which are substantially equivalent in construction and operation to valve means 3 and support 16 described above. The drying chamber is also provided with a steam jacket 54 supplied with steam through valve 55 and itself provided with a trap 56 for the removal of condensates. Preferably, the same steam pressure is used as in the sterilizing chamber so that the components leave the drying chamber at or near the sterilization temperature. Air is circulated through the drying chamber by means of circulatory duct 57, which is provided with a fan 58, an air heater 59 and a condenser 60. Any liquid falling to the base of the drying chamber is drawn off through the drainage duct 61 in valve means 52.

In this second embodiment of the apparatus of the invention, control means 50 (representative connections for which are shown schematically in FIG. 2) operates to ensure that valve means 3 and 52 are not simultaneously open thereby maintaining a bacteriological barrier between the cleaning and the sterilizing chambers. The three chambers can if desired be operated simultaneously. However, before transfer of a charge of components from the cleaning or drying chambers, the subsequent chambers, i.e. the drying and sterilizing chambers respectively, must of course first be discharged.

Figure 3:
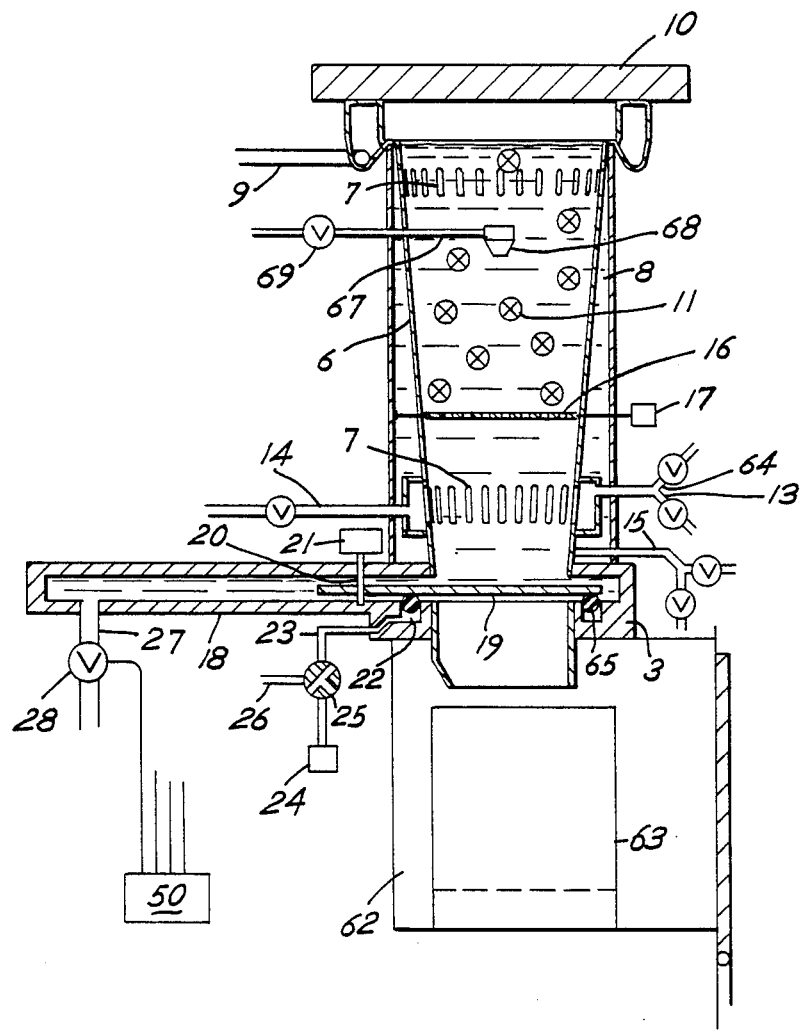
FIG. 3 is a schematic cross-sectional view of one embodiment of a cleaning apparatus according to the present invention.

FIG. 3 illustrates an embodiment of a cleaning apparatus according to the invention. Again, elements similar to those illustrated in the earlier figures are similarly numbered. It will be seen therefore that the apparatus of FIG. 3 comprises a cleaning chamber essentially similar to the cleaning chambers of the apparatus of FIGS. 1 and 2 but which discharges via valve means 3 directly into a receiving chamber 62. The receiving chamber preferably comprises a removable bin 63 with an apertured inner base to allow for drainage of the cleaned components. The bin may be removed to take the cleaned components to separate apparatus for further processing, for example sterilization. Alternatively, valve means 3 may discharge directly into the component receiving compartment of a further piece of component processing apparatus or onto a feed mechanism, for example a conveyor, leading to such further apparatus.

Typically the apparatus of the invention might have an hourly throughput for conventionally sized containers closures of the order of 5000 to 20000 pieces.

It will be appreciated that while the present invention has been described in terms of apparatus for cleaning pharmaceutical container components it might also be used for the cleaning of other items for use in the medical, veterinary, dental or pharmaceutical industries.

I claim:

1. A pharmaceutical container component cleaning apparatus comprising a first chamber having a base arranged to receive pharmaceutical container components for cleaning and a cleaning medium, a second chamber arranged to sterilize pharmaceutical container components cleaned in said first chamber and provided with sterilizing means, valve means located at the base of said first chamber and openable to permit transfer of cleaned components from said first chamber to said second chamber and closeable to provide a bacteriological barrier between said first and second chambers, said valve means comprising a displaceable valve plate, a displaceable annular seal member, valve plate displacing means operable to move said valve plate between an open position permitting passage of components through the valve means and a closed position preventing such passage, and seal member displacing means operable to urge said seal member into sealing engagement with said valve plate when said valve plate is in its closed position, and further comprising a conduit arranged between said valve means and said second chamber and provided with means for establishing a pressure differential along said conduit whereby to cause cleaned components passing through said valve means to be urged along said conduit towards said second chamber.

2. Apparatus as claimed in claim 1 wherein said means for establishing a pressure differential comprises a vacuum pump.

3. Apparatus as claimed in claim 2 further comprising means for heating said conduit.

4. Apparatus as claimed in claim 3 wherein the conduit is elongated and at least part of the length of said conduit extends in an upward direction relative to the horizontal.

5. Apparatus as claimed in claim 1 comprising a further valve means operable to permit discharge of sterilized components from said second chamber.

6. Apparatus as claimed in claim 1 further provided in a said first chamber with a permeable component support member which is displaceable to permit discharge of components from said chamber.

7. Apparatus as claimed in claim 1 comprising at least three selectively interconnectible chambers with valve means provided between each mutually interconnectible pair of chambers, said valve means being openable to permit passage of components between adjacent chambers and closeable to provide a bacteriological barrier between adjacent chambers, a first of said chambers being provided with said cleansing means and a second of said chambers being provided with said sterilizing means.

8. Apparatus as claimed in claim 7 wherein a third of said chambers is arranged to receive cleaned components from said first chamber and is provided with drying means, and wherein said second chamber is arranged to receive dried components from said third chamber.

9. Apparatus as claimed in claim 8 further comprising valve control means arranged to control the operation of said valve means and thereby to maintain a bacteriological barrier between said first and second chambers.

10. Apparatus as claimed in claim 1 wherein said valve plate and said seal member are displaceable in mutually perpendicular directions.

11. Apparatus as claimed in claim 10 wherein said first chamber is provided with a drainage duct arranged to drain cleaning medium in said first chamber away from said valve means.

12. A pharmaceutical container component cleaning apparatus comprising a first chamber having a base arranged to receive pharmaceutical container components for cleaning and a cleaning medium, a second chamber arranged to receive pharmaceutical container components cleaned in said first chamber, and valve means located at the base of said first chamber and openable to permit transfer of cleaned components from said first chamber to said second chamber and closeable to provide a bacteriological barrier between said first and second chambers, said valve means comprising a displaceable valve plate, a displaceable annular seal member, valve means comprising a displaceable valvae plate, a displaceable annular seal member, valve plate displacing means operable to move said valve plate between an open position permitting passage of components through the valve means and a closed position preventing such passage, and seal member displacing means operable to urge said seal member into sealing engagement with said valve plate when said valve plate is in its closed position, and further comprising conduit means arranged between said valve means and said second chamber and provided with means for establishing a pressure differential along said conduit means whereby to cause cleaned components passing through said valve means to be urged along said conduit towards said second chamber.

13. Apparatus as claimed in claim 12 wherein said valve plate and said seal member are displaceable in mutually perpendicular directions.

14. Apparatus as claimed in claim 13 wherein said first chamber is provided with a drainage duct arranged to drain cleaning medium in said first chamber away from said valve means.

* * * * *